(12) United States Patent
Meoli et al.

(10) Patent No.: US 6,719,994 B2
(45) Date of Patent: Apr. 13, 2004

(54) INHALATORY COMPOSITIONS OF FORMOTEROL

(75) Inventors: Andrea Meoli, Cagiallo (CH); Alessandro Cagnoni, Lavena Ponte Tresa (IT); Sereno Vanossi, Rovio (CH)

(73) Assignee: Chemo Healthcare S.A., Lugano-Cassarate (CH)

( * ) Notice: Subject to any disclaimer, the term of this patent is extended or adjusted under 35 U.S.C. 154(b) by 0 days.

(21) Appl. No.: 10/086,868

(22) Filed: Mar. 4, 2002

(65) Prior Publication Data

US 2002/0155068 A1 Oct. 24, 2002

(30) Foreign Application Priority Data

Mar. 2, 2001 (IT) ...................... MI2001A0428

(51) Int. Cl.⁷ ............................. A61F 13/00; A61K 9/14
(52) U.S. Cl. ........................ 424/434; 424/489; 424/499
(58) Field of Search ................................ 424/401, 434, 424/489, 499; 514/423, 171

(56) References Cited

U.S. PATENT DOCUMENTS

| 5,263,475 | A | * | 11/1993 | Altermatt et al. | ....... | 128/203.15 |
| 5,525,623 | A | * | 6/1996 | Spear et al. | ................. | 514/423 |
| 5,637,620 | A | * | 6/1997 | Trofast et al. | ............... | 564/630 |
| 5,674,860 | A | * | 10/1997 | Carling et al. | ............... | 514/171 |
| 5,965,622 | A | * | 10/1999 | Senanayake | ................. | 514/653 |

FOREIGN PATENT DOCUMENTS

WO       WO 9917754 A1  *  4/1999  ............ A61K/9/72

* cited by examiner

*Primary Examiner*—Thurman K. Page
*Assistant Examiner*—Micah-Paul Young
(74) *Attorney, Agent, or Firm*—Young & Thompson

(57) ABSTRACT

Inhalatory pharmaceutical compositions containing Formoterol as active ingredient, comprising:
  a vial containing a sterile liquid vehicle suitable for inhalation;
  a reservoir chamber cap containing a powder mixture consisting of Formoterol or a related salt in micronized form and one or more excipients, soluble in the vehicle and suitable for respiratory use.

12 Claims, No Drawings

INHALATORY COMPOSITIONS OF FORMOTEROL

The present invention relates to pharmaceutical compositions for the administration to the lungs of Formoterol in aqueous solution.

BACKGROUND OF THE INVENTION

The inhalation therapy in the field of respiratory tract diseases includes different methods for the administration of the drug to the lungs. The aerosol can be obtained by nebulization of the product from a pressurized metered dose inhaler, by dispersion of a dry powder with suitable devices and by mechanical or ultrasound atomization of aqueous solutions or suspensions.

The currently used formulations contain excipients physiologically compatible with the bronchial epithelium, usually consisting of co-solvents, preservatives, chelating agents, pH regulators and surfactants.

In the case of solution products, the respirable fraction is determined by the atomization efficiency and by the size of the aerosol particles produced by the nebulizing equipment. In the case of suspensions, the respirable fraction is determined also by the particle size of the used micronized active ingredient.

A characteristic of some active ingredients is the poor chemical (degradation) or physical (crystal morphological changes) stability in solution or suspension. As a consequence, the shelf life of the finished product upon storage in normal ambient condition, and sometime even in refrigerator, is insufficient.

Formoterol is a drug belonging to the class of beta2-agonists, characterized by rapid onset of broncho-dilating action which lasts for many hours. For the treatment of asthma, Formoterol is usually administered through the inhalatory route by means of the so called dry powder inhalers (DPI), storable under normal ambient conditions, or in form of suspensions or solutions by means of pressurized metered dose inhalers, which should be stored in refrigerator, in view of the above discussed poor stability of the active ingredients in aqueous medium.

The stability problem of active ingredients in solutions may also be solved by a conventional technology adopted in the pharmaceutical and para-pharmaceutical fields, based on reservoir container systems designed for the reconstitution of solution immediately before use, wherein a liquid component (solvent) and a solid component (soluble material) are placed in separate compartments.

Two basic problems are met if this technology is considered for Formoterol formulations for the inhalatory use. The first is the possibility to dose the quantity of active ingredient with sufficient precision. The standard dose of Formoterol is within the range of some tens of micrograms, usually about 12 micrograms: with the current technology it is quite impossible to dose such quantities with sufficient precision in industrial processes. This problem can be by-passed by the method disclosed in WO 99/17754, consisting in the dissolution of the active ingredient and solid excipients in wter, filling of solution in a reservoir container and followed by freeze drying in order to obtain a solid state open matriz network. The other problem is that the excipients have to be chosen only among those approved for the respiratory use, with demonstrated tolerability on the respiratory tract.

The present invention solves the problems concerning active ingredient stability, dosage uniformity and tolerability of the formulation to the lungs, by applying the technology of capsule production to the container system for the extemporaneous reconstitution of a solution immediately before use.

DESCRIPTION OF THE INVENTION

The invention provides pharmaceutical compositions for the inhalatory use comprising Formoterol in dry powder form.

The compositions of the invention comprise:
 a vial containing a sterile liquid vehicle suitable for inhalation;
 a reservoir chamber cap containing a powder mixture consisting of Formoterol or a related salt in micronized form and one or more excipients, soluble in the vehicle and suitable for respiratory use. A barrier of suitable material that has the function to maintain the solid component separated from the liquid component delimits this chamber caps. The caps also have a mechanism in order to easily remove or break this separation.

Immediately before the use, the patient breaks the barrier and shakes the container so as to contact the two components (liquid and solid).

The excipients of the solid component dissolve in the liquid and Formoterol is dissolved or suspended in the liquid, depending on the composition of the liquid component. After this step, the vial can be opened and the mixture is transferred into the nebulizer equipment, for inhalation according to the instructions of each device, which may be air-driven or ultrasound-driven.

This container system is suitable for delivering both single dose and multidose. In this case the container must be closed again after delivery of the first dose and stored in refrigerator for subsequent use.

The system of the invention is also useful for combinations of Formoterol with other active ingredients, such as Budesonide, Fluticasone, Mometasone, Flunisolide, Ipratropium bromide and others that can be in solution in the liquid component or in the solid component mixed with the others solid excipients.

The extemporaneously prepared product showed very good stability for the period of administration that, normally, last no longer than 15 minutes.

In case of product in suspension, the preferred size of the active ingredient crystals is that normally used for respiratory powders, namely less than 10 microns, preferably 1 to 5 microns, that is the range usually required for respiratory products.

In case of product for dissolution in the liquid component, tests were performed with both micronized crystalline active ingredient and active ingredient premixed with the other excipients (for instance lactose) and dissolved in a suitable solvent. After that, a powder easily soluble in the liquid component was obtained by means of spray dry technology.

In both cases the "in vitro" respirable fraction values obtained were similar to those of other products marketed in the form of inhalatory solution or suspension (15–25%).

The liquid vehicle contained in the vial is preferably sterile water, which may be added with co-solvents and other excipients, for example preservative and surfactants, such as cetostearyl alcohol, polysorbate 80, sorbitan trioleate and cetyl pyridinium chloride. Examples of co-solvents are ethanol and propylene glycol.

Preferred surfactants are cetostearyl alcohol and polysorbate 80, in quantity from 0.01 to 0.5% w/w.

A preferred co-solvent is propylene glycol in amounts from 10 to 50%, preferably from 20 to 40%.

The isotonicity of the solution may be adjusted by addition of a suitable quantity of sodium chloride to the liquid component, to improve physiological tolerance.

Formoterol is used in the formulations of the invention preferably as fumarate, in a dose range from 5 to 25 micrograms.

The solid excipients mixed with Formoterol include saccharides, amino acids and other components suitable for respiratory use. Preferred excipients are lactose, mannitol, glucose and isoleucine in quantity from 5 to 200 mg per dose.

Therefore, the invention solves the problem of product instability, since the active ingredient remains in solution or suspension for the time of administration only.

Another aspect of the invention is related to the application of capsules filling technology currently used for the production of respiratory powder in capsules. The homogeneous mix of solid excipient and active ingredient may be dosed in the reservoir in a precise quantity, e.g. from 5 to 200 mg, preferably 24 mg. This technology solves the problem of dosage uniformity.

The problem of components compatibility is solved by suitably selecting excipients of current use in respiratory products. In particular, lactose monohydrate is widely used in dry powder inhalatory formulations.

The present invention also relates to a method for the preparation of the formulation according to the previous claims, wherein micronized Formoterol is homogeneously mixed with the powder excipients, the resulting mix is filled in the reservoir caps and the reservoir caps are placed on the vials previously filled with the liquid component.

The following examples illustrate the invention in greater detail.

EXAMPLES:

| Powder component | | Liquid component | |
|---|---|---|---|
| Formoterol fumarate | 15 μg | Water | 3 ml |
| Lactose monohydrate | 25 mg | Sodium chloride | 25 mg |
| Formoterol fumarate | 15 μg | Water | 3 ml |
| Lactose monohydrate | 50 mg | Polysorbate 80 | 6 mg |
| Formoterol fumarate | 15 μg | Water | 3 ml |
| Lactose monohydrate | 50 mg | Cetostearyl alcohol | 9 mg |
| Formoterol fumarate | 15 μg | Water | 2 ml |
| Lactose monohydrate | 150 mg | Propylene glycol | 1 g |
| | | Polysorbate 80 | 6 mg |

What is claimed is:

1. A pharmaceutical inhalation delivery device, comprising:
    a pharmaceutical composition for the inhalatory use, containing powder Formoterol as active ingredient;
    a vial containing a sterile aqueous vehicle suitable for the respiratory administration; and
    a reservoir cap containing a homogeneous mix of Formoterol powder or the salts thereof, in micronized form and one or more solid excipients suitable for the respiratory use.

2. The pharmaceutical inhalation delivery device according to claim 1, wherein Formoterol is in the form of fumaric acid salt.

3. The pharmaceutical inhalation delivery device according to claim 2, wherein the vehicle consists of water and sodium chloride, optionally mixed with propylene glycol, ethanol, surfactants and preservatives.

4. The pharmaceutical inhalation delivery device according to claim 3, wherein the surfactant is polysorbate 80 or cetostearyl alcohol.

5. The pharmaceutical inhalation delivery device according to claim 4, wherein the powder excipient is selected from lactose, mannitol, glucose and isoleucine.

6. The pharmaceutical inhalation delivery device according to claim 1, wherein the pharmaceutical inhalation delivery device used for extemporaneous solution is a unit dose or multiple dose.

7. The pharmaceutical inhalation delivery device according to claim 1, wherein a further active ingredient is combined with Formoterol in the powder mix and placed in the reservoir.

8. The pharmaceutical inhalation delivery device according to claim 1, wherein a further active ingredient is combined with Formoterol and it is present in suspension or solution in the liquid component of the pharmaceutical inhalation delivery device.

9. The pharmaceutical inhalation delivery device according to claim 7, wherein the active ingredient combined with the Formoterol is Budesonide, Fluticasone, Flunisolide, Mometasone or Ipratropium bromide.

10. A method for the preparation of a pharmaceutical inhalation delivery device according to claim 1, wherein micronized Formoterol is homogeneously mixed with the powder excipients, the resulting mix is filled in the reservoir caps and the reservoir caps are placed on the vials previously filled with the liquid component.

11. A method of preparing a pharmaceutical inhalation delivery device, comprising the steps of:
    providing a vial containing a sterile aqueous vehicle suitable for respiratory administration;
    homogeneously mixing micronized Formoterol with powdered excipients suitable for respiratory use to produce a resulting mixture; and
    filling reservoir caps with the resulting mixture and placing the filled reservoir caps within the sterile aqueous vehicle.

12. The method of claim 11, wherein the Formoterol includes Formoterol powder or salts thereof.

* * * * *